United States Patent [19]

Tai

[11] Patent Number: 4,757,155

[45] Date of Patent: Jul. 12, 1988

[54] PROCESS FOR THE PREPARATION OF OPTICALLY ACTIVE 2-[4-(2',4'-DIHALOPHENOXY)PHENOXY]-PROPIONIC ACIDS

[75] Inventor: Jimmy J. Tai, Midland, Mich.

[73] Assignee: The Dow Chemical Company, Midland, Mich.

[21] Appl. No.: 945,427

[22] Filed: Dec. 22, 1986

[51] Int. Cl.$^4$ ............................................. C07B 57/00
[52] U.S. Cl. ...................................... 562/401; 560/61; 560/62; 562/472
[58] Field of Search .................. 562/401, 472; 560/62, 560/61

[56] References Cited

U.S. PATENT DOCUMENTS

| | | | |
|---|---|---|---|
| 4,035,416 | 7/1977 | Brust | 562/472 |
| 4,173,709 | 11/1979 | Metivier et al. | 562/471 |
| 4,309,547 | 1/1982 | Koch et al. | 562/472 X |
| 4,532,346 | 7/1985 | Rehn et al. | 562/471 |

FOREIGN PATENT DOCUMENTS 0192849 9/1986 European Pat. Off. .
2486071 1/1982 France .

Primary Examiner—Werren B. Lone
Assistant Examiner—Vera C. Clarke
Attorney, Agent, or Firm—S. Preston Jones; Ronald G. Brookens

[57] ABSTRACT

A process for the preparation of optically active 2-[4-(2',4'-dihalophenoxy)phenoxy]propionic acids of at least 75 percent enantiomeric excess of the desired optical isomer which comprises contacting a 2-chloropropionic acid or a lower alkyl ester or an alkali metal salt thereof, having an optical purity of greater than 90 percent of the opposite configuration, with from 2 to 10 molar equivalents of a 4-(2',4'-dihalphenoxy)phenol in an aqueous base.

5 Claims, No Drawings

PROCESS FOR THE PREPARATION OF OPTICALLY ACTIVE 2-[4-(2',4'-DIHALOPHENOXY)PHENOXY]PROPIONIC ACIDS

BACKGROUND OF THE INVENTION

The herbicidal activity of various halogenated 4-phenoxy-phenoxy-propionic acids is well known in the art. For example, U.S. Pat. No. 3,954,442 specifically discloses the herbicidal utility of 2-[4-(2'-hydrogen or chloro-4'-chlorophenoxy)phenoxy]propionic acids and certain derivatives thereof. Similarly, U.S. Pat. Nos. 4,370,489 and 4,550,192 describe the even better herbicidal effect of 2-[4-(2'-chloro-4'-bromophenoxy)-phenoxy]propionic acid and 2-[4-(2'-fluoro-4'-halophenoxy)phenoxy]propionic acids and their agriculturally acceptable derivatives, respectively.

Optical isomers are often known to have enhanced biological activity over the corresponding racemates. For example, U.S. Pat. No. 4,531,969 has demonstrated that the R-enantiomers of many 2-(4-phenoxyphenoxy)-propionic acids are distinguished by a considerably enhanced herbicidal action compared with the racemates. Therefore, the application of mixtures enriched in the more efficacious R-enantiomer offers both economical and environmental advantages, since reduced quantities of herbicide are required to achieve comparable control.

Various methods for obtaining high concentrations of optical isomers are known. In addition to the resolution of a racemic mixture into its optically active components which, for example, depends on the conversion to diastereomers and subsequent physical separation, individual enantiomers can be obtained by direct synthesis employing an appropriate optically active starting material. For example, optically active 2-substituted propionic acids are conveniently prepared by the reaction of either an optically active 2-halopropionic acid or an optically active alkyl or aryl sulfonate of lactic acid with an appropriate nucleophile. Such nucleophilic displacement reactions generally occur with inversion of configuration of the asymmetric carbon atom of the starting material. Therefore, to prepare the R-enantiomer of the 2-substituted propionic acid, the S-enantiomer of the 2-halopropionic acid or sulfonate ester of lactic acid is employed as the starting material.

Theoretically, one can obtain essentially 100 percent of the desired enantiomer by this method. In practice, however, the optical purity of the final product is largely determined by (a) the optical purity of the starting material, (b) the nature of the leaving group, and (c) the specific conditions employed. Typically, one obtains products containing a ratio of from 70 to 90 percent of the desired enantiomer and, correspondingly, 10 to 30 percent of the other optical isomer. Such products are then said to possess an optical purity of 40 to 80 percent, i.e., from 40 to 80 percent of the mixture is the desired enantiomer and from 20 to 60 percent is a racemic mixture.

The importance of the nature of the leaving group in the starting propionic acid is illustrated in the article of G. Sakata et al. in J. Pesticide Sci., 10, 69–73 (1985). Product of the following optical purities were obtained with different leaving groups under comparable conditions: tosylate (~80 percent); mesylate (~45 percent); bromide (~45 percent); and chloride (~10 percent). Thus, although optically active 2-chloropropionic acid derivatives may be the most preferable starting material from the viewpoint of cost and availability, they are the least advantageous with respect to optical purity of the product.

Similarly, the importance of the reaction conditions is well known. For example, as shown in U.S. Pat. No. 4,532,328, the optical purity of the final product can be substantially enhanced by employing a 5 to 20 fold molar excess of the optically active starting material. Although enhanced optical yields are achieved, large amounts of relatively expensive optically active reagents such as S-methyl 2-chloropropionate must be recovered and recycled. Furthermore, this reagent may be susceptible to racemization under the reaction and recovery conditions thus precluding its direct recycle in the process.

SUMMARY OF THE INVENTION

The present invention provides a process for making optically active 2-(4-phenoxyphenoxy)propionic acids of formula I

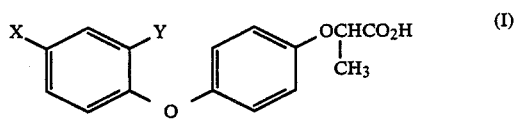

of enhanced optical purity of at least 75 percent which comprises contacting one equivalent of an optically active 2-chloropropionic acid, a $C_1$–$C_4$ lower alkyl ester or an alkali metal salt thereof with a stoichiometric excess of a 4-phenoxyphenol of formula II

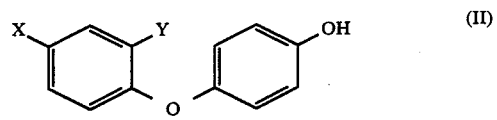

wherein
in formula I and II X is fluorine, chlorine, bromine or iodine, and Y is hydrogen, fluorine, chlorine, bromine or iodine in the presence of an aqueous base.

It is well understood that such reactions occur with inversion of the configuration of the asymmetric center of the chloropropionic acid starting material. For example, the S-form of the 2-chloropropionic acid starting material is required to produce the R-form of the product.

The enhanced optical purity of the product is related to the amount of phenoxyphenol used in excess of one molar equivalent. In order to achieve optical purities exceeding 75 percent of a particular enantiomer, it is necessary to employ at least 2 equivalents of phenoxyphenol and a 2-chloropropionic acid derivative containing at least a 90 percent excess of the appropriate enantiomer (95:5).

The upper range of the amount of phenoxyphenol to be used is generally determined by an evaluation of the degree of optical purity of the product which is desired and the incremental cost of recovering and recycling the excess phenoxyphenol. Typically, amounts of phenoxyphenol in the range of 2 to 10 molar equivalents per mole of 2-chloropropionic acid, ester or salt are desired. Preferably, amounts in the range of 2 to 5 molar equivalents are employed.

The excess of phenoxyphenol is advantageously recovered during the reaction workup. For example, by adjusting the pH of the alkaline reaction mixture with acid so that the phenate is converted to the phenol while the desired carboxylic acid remains as the water-soluble salt form, the phenoxyphenol can be recovered by extraction with an organic solvent.

With this approach, the optically active starting material is essentially completely consumed. Thus, racemization associated with recovery and recycle of the optically active reagent is avoided. Thus the present invention avoids the shortcomings of the prior art in the utilization of 2-chloropropionic acid and its derivatives for preparing optically active 2-(4-phenoxyphenoxy)-propionic acids.

Furthermore, the process of this invention is conducted in an aqueous medium, thus obviating the need for polar aprotic organic solvents or azeotropic drying procedures typically employed for such reactions.

The reaction is generally carried out at atmospheric pressure. However, operation at reduced or elevated pressures is equally operable.

Similarly, the reaction can be conducted from ambient temperature to the reflux temperature of the mixture, but the range of about 60° to about 90° C. is preferred.

When using the lower alkyl esters of 2-chloropropionic acid as the starting material, the alkali metal salt of the product is obtained under the reaction conditions by saponification. Similarly, the free acid itself is neutralized to the alkali metal salt. Therefore, sufficient base must be added to allow for neutralization of the acid or saponification of the ester in addition to that necessary to stoichiometrically convert the phenoxyphenol to the corresponding phenate. Generally, the one molar equivalent of base necessary to achieve total saponification or neutralization of the propionate in addition to the one molar equivalent required to ionize all of the phenoxyphenol present or a 5 to 30 percent excess of the total amount is desirable.

Any base sufficiently strong to substantially ionize the phenoxyphenol without interfering with the reaction or subsequent workup is contemplated. Such bases include the alkali metal (Li+, Na+, K+) carbonates and hydroxides with sodium and potassium hydroxide being the most preferred.

After completion of the reaction, the mixture is alkaline. By adjusting the pH of the mixture to substantially convert the excess phenate to the phenol while maintaining the product in the form of the alkali metal salt, the excess phenoxyphenol can be recovered in substantially pure form by extraction with an immiscible organic solvent. Such solvents include chlorinated hydrocarbons e.g., methylene chloride or perchloroethylene, aromatics e.g., chlorobenzene and ketones e.g., methyl isobutyl ketone. The phenoxyphenol, suitable for recycle in the process, can be recovered by evaporation of the solvent.

After removal of the excess phenoxyphenol, the pH of the remaining aqueous reaction mixture is typically adjusted with a strong mineral acid, e.g. HCl or $H_2SO_4$ to convert the product to the free acid form. The 4-phenoxy-phenoxy-propionic acid of high optical purity can be obtained by extraction with an immiscible organic solvent, preferably the same solvent used to recover the phenoxyphenol, followed by evaporation of that solvent.

The free acids of formula I are preferably esterified employing conventional ester formation procedures to produce agriculturally acceptable esters which include, for example, the following: methyl, ethyl, propyl, butyl, octyl, ethoxyethyl, butoxyethyl, and methoxypropyl.

DETAILED DESCRIPTION OF THE INVENTION

EXAMPLE 1

Preparation of R-2-[4-(2'-fluoro-4'-bromophenoxy)phenoxy]propionic acid

To 14.15 grams (g) (0.05 mole) of 4-(2'-fluoro-4'-bromophenoxy)phenol in a flask equipped with a mechanical stirrer, condenser, addition funnel and heating mantle was added 12 g (0.075 mole) of 25 percent NaOH. The solution was then heated to 65° C. and 3.0 g (0.025 mole) of S-methyl 2-chloropropionate of 98 percent optical purity was added to the reaction mixture. The reaction mixture was heated to 85° C. and stirred for 30 minutes. After cooling to room temperature, the pH of the solution was adjusted to approximately 9.0 with hydrochloric acid. Methyl iso-butyl ketone was used to extract the unreacted 4-(2'-fluoro-4'-bromophenoxy)phenol which was subsequently recovered by evaporation of the solvent. The pH of the aqueous phase was further adjusted to about 5.0 with hydrochloric acid. Methyl iso-butyl ketone was again used to extract the product. After evaporating the solvent, 5.6 g of R-2-[4-(2'-fluoro-4'-bromophenoxy)phenoxy]propionic acid was obtained with a melting point of 77°–80° C. The nuclear magnetic resonance spectrum was consistent with the structure. The enantiomer ratio of R to S was found to be 88 to 12 (76 percent optical purity) by capillary gas chromatography on a DB-1 column after derivatization with S(+)-2-aminopropanol.

EXAMPLE 2

Preparation of S-2-[4-(2'-chloro-4'-bromophenoxy)phenoxy]propionic acid

To 14.4 g (0.05 mole) of 4-(2'-chloro-4'-bromophenoxy)phenol in a flask equipped with a mechanical stirrer, condenser, addition funnel and heating mantle was added 12.8 g (0.08 mole) of 25 percent NaOH. The solution was then heated to 65° C. and 2.94 g (0.024 mole) of 99 percent optically pure R-methyl 2-chloropropionate was added to the reaction mixture. The reaction mixture was heated to 85° C. and stirred for 30 minutes. After cooling to room temperature, the pH of the solution was adjusted to approximately 9.0 with hydrochloric acid. Methyl iso-butyl ketone was used to extract the unreacted 4-(2'-chloro-4'-bromophenoxy)-phenol which was subsequently recovered by evaporation of the solvent. The pH of the aqueous phase was further adjusted to about 5.0 with hydrochloric acid. Methyl iso-butyl ketone was again used to extract the product. After evaporating the solvent, 7.7 g of crude S-2-[4-(2'-chloro-4'-bromophenoxy)phenoxy]propionic acid was obtained. The nuclear magnetic resonance spectrum was consistent with the structure and indicated the presence of residual methyl iso-butyl ketone. The enantiomer ratio of R to S was found to be 11 to 89 (78 percent optical purity) by capillary gas chromatography after derivatization with S(+)-2-aminopropanol.

EXAMPLE 3

Preparation of R-2-[4-(2'-fluoro-4'-iodophenoxy)phenoxy]propionic acid

In a flask equipped with a stirrer, condenser, addition funnel and heating mantle, 2.4 g (0.0073 mole) of 4-(2'-fluoro-4'-iodophenoxy)phenol were dissolved in 2.09 g (0.0131 mole) of 25 percent NaOH at 80° C. Thereafter, 0.43 g (0.0035 mole) of 90 percent optically pure S-methyl 2-chloropropionate were added and the reaction mixture was maintained at 80° C. for 2 hours. Approximately 10 ml of water were added to the mixture which was cooled to ambient temperature. The pH was adjusted to 9.0 with hydrochloric acid and methyl isobutyl ketone was used to extract the unreacted 4-(2'-fluoro-4'-iodophenoxy)phenol which was recovered by evaporation of the solvent. The pH of the aqueous phase was further adjusted to approximately 1.0. Methyl iso-butyl ketone was again used to extract the product. After evaporation of the solvent, 0.5 g of crude R-2-[4-(2'-fluoro-4'-iodophenoxy)phenoxy)propionic acid was obtained. The nuclear magnetic resonance spectrum was consistent with the structure and indicated the presence of residual methyl iso-butyl ketone. The enantiomer ratio of R to S was found to be 89 to 11 (78 percent optical purity) by capillary gas chromatography after derivatization with S(+)-2-aminopropanol.

EXAMPLE 4

Preparation of R-2-[4-(2'-fluoro-4'-bromophenoxy)phenoxy]propionic acid

The process of Example 1 was repeated using 10.0 g (0.0353 mole) of 4-(2'-fluoro-4'-bromophenoxy)phenol, 2.4 g (0.0429 mole) KOH, 6.5 g of $H_2O$ and 0.86 g (0.0072 mole) of 90 percent optically pure S-methyl 2-chloropropionate. After workup 2.0 g of crude R-2-[4-(2'-fluoro-4'-bromophenoxy)phenoxy]propionic acid was obtained having an optical purity of 80 percent.

EXAMPLE 5

Preparation of R-methyl 2-[4-(2'-fluoro-4'-bromophenoxy)phenoxy]propionate

To 2.0 g of R-2-[4-(2'-fluoro-4'-bromophenoxy)-phenoxy]propionic acid (80 percent optical purity) in a flask equipped with a thermometer, stirrer and condenser was added 20 ml of methanol, 0.5 g of Dowex ®MSC-1 H+ ion exchange resin and 0.8 g of 2,2-dimethoxypropane. The mixture was heated at reflux for 10 hours at which time less then 1 percent free acid remained. The mixture was cooled and the resin catalyst was removed by filtration. After evaporation of the volatile components, 1.9 g of R-methyl 2-[4-(2'-fluoro-4'-bromophenoxy)phenoxy)propionate of 78.6 percent optical purity was obtained.

Various modifications may be made in the present invention without departing from the spirit or scope thereof, and it is understood that I limit myself only as defined in the appended claims.

What is claimed is:

1. A process for the preparation of optically active 2-(4-phenoxyphenoxy)propionic acids of the formula

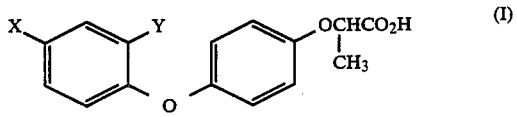

(I)

wherein X is fluorine, chlorine, bromine or iodine, and Y is hydrogen, fluorine, chlorine, bromine or iodine of at least 75 percent enantiomeric excess of the desired optical isomer which comprises contacting 2-chloropropionic acid, a $C_1$-$C_4$ lower alkyl ester or an alkali metal salt thereof, having an optical purity greater than 90 percent of the opposite configuration, with from 2 to 10 molar equivalents of a 4-phenoxyphenol of the formula

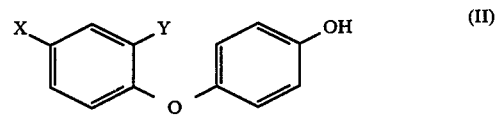

(II)

wherein
X is fluorine, chlorine, bromine or iodine, and Y is hydrogen, fluorine, chlorine, bromine or iodine in an aqueous base.

2. A process of claim 1 wherein the 2-chloropropionic acid derivative is of the S-configuration and the product is of the inverted R-configuration.

3. A process of claim 1 wherein the base is sodium or potassium hydroxide.

4. A process of claim 1 wherein 2 to 5 molar equivalents of a 4-phenoxyphenol are employed.

5. A process according to claim 1 wherein the optically active product in the free acid form is subsequently esterified to produce an alkyl or alkoxyalkyl ester of from 1 to 8 carbon atoms.

* * * * *